US00PP33643P2

(12) United States Plant Patent
Mukundan

(10) Patent No.: US PP33,643 P2
(45) Date of Patent: Nov. 16, 2021

(54) ***SPATHIPHYLLUM* PLANT NAMED 'MUKJESS'**

(50) Latin Name: ***Spathiphyllum* Schott.**
Varietal Denomination: Mukjess

(71) Applicant: K.S.G.'s FARM & NURSERY, Tamil Nadu (IN)

(72) Inventor: Parthasarathy Mukundan, Tamil Nadu (IN)

(73) Assignee: K.S.G.'s FARM + NURSERY, Chennai (IN)

( * ) Notice: Subject to any disclaimer, the term of this patent is extended or adjusted under 35 U.S.C. 154(b) by 0 days.

(21) Appl. No.: 16/926,252

(22) Filed: Jul. 10, 2020

(51) Int. Cl.
*A01H 5/02* (2018.01)
*A01H 6/00* (2018.01)
*A01H 5/10* (2018.01)
*A01H 6/14* (2018.01)

(52) U.S. Cl.
USPC ..... Plt./364
CPC ..... *A01H 6/00* (2018.05); *A01H 5/10* (2013.01); *A01H 6/14* (2018.05)

(58) Field of Classification Search
USPC ..... Plt./364
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Spathiphyllum* plant named 'Mukjess', characterized by its relatively compact, upright, outwardly arching and uniform plant habit; moderately vigorous growth habit; variegated leaves that are yellow green to greyed green-in color with dark green-colored venation and margins; if present, white-colored spathes are positioned above the foliar plane on strong and erect scapes; and good interiorscape performance.

3 Drawing Sheets

Figure 1:
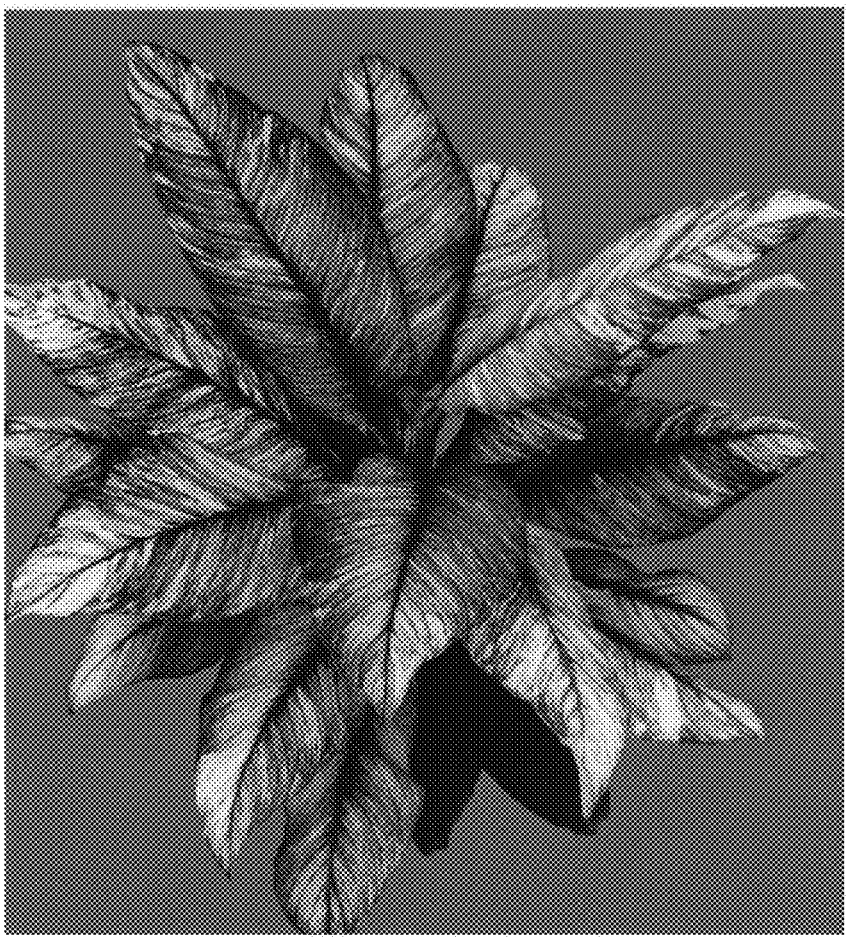

Botanical designation: *Spathiphyllum* Schott.
Cultivar denomination: 'MUKJESS'.

BACKGROUND OF THE INVENTION

The present invention relates to a new and distinct cultivar of *Spathiphyllum* plant, botanically known as *Spathiphyllum* Schott. and hereinafter referred to by the cultivar name 'Mukjess'.

The new *Spathiphyllum* plant is a product of a controlled breeding program conducted by the Inventor in Tiruporur, Tamil Nadu, India. The objective of the breeding program is to create new *Spathiphyllum* plants with unique leaf variegation patterns and good postproduction longevity.

The new *Spathiphyllum* plant is a naturally-occurring whole plant mutation of an unnamed variegated selection of *Spathiphyllum* Schott., not patented. The unnamed variegated selection (mutation parent) is a whole plant mutation of non-variegated *Spathiphyllum* Schott. 'Gorgusis No. 1', disclosed in U.S. Plant Pat. No. 6,964. The new *Spathiphyllum* plant was discovered and selected by the Inventor as a single plant from within a population of plants of the mutation parent in a controlled greenhouse environment in Tiruporur, Tamil Nadu, India on Sep. 21, 2012.

Asexual reproduction of the new *Spathiphyllum* plant by divisions in a controlled environment in Tiruporur, Tamil Nadu, India since Jan. 12, 2014 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mukjess'. These characteristics in combination distinguish 'Mukjess' as a new and distinct *Spathiphyllum* plant:

1. Relatively compact, upright, outwardly arching and uniform plant habit.
2. Moderately vigorous growth habit.
3. Variegated leaves that are yellow green to greyed green-in color with dark green-colored venation and margins.
4. If present, white-colored spathes are positioned above the foliar plane on strong and erect scapes.
5. Good interiorscape performance.

Plants of the new *Spathiphyllum* differ from plants of the mutation parent selection in the following characteristics:

1. Plants of the new *Spathiphyllum* are more compact and slower-growing than plants of the mutation parent selection.
2. Leaves of plants of the new *Spathiphyllum* are smaller than leaves of plants of the mutation parent selection.
3. Plants of the new *Spathiphyllum* have variegated leaves that are yellow green to greyed green-in color with dark green-colored venation and margins whereas plants of the mutation parent have variegated leaves that have large random and irregular sectors that are white, greyed green or dark green in color with green and white-colored midveins.

Plants of the new *Spathiphyllum* can also be compared to plants of *Spathiphyllum* Schott. 'Domino', disclosed in U.S.

Plant Pat. No. 9,944. In side-by-side comparisons, plants of the new *Spathiphyllum* differ from plants of 'Domino' in the following characteristics:

1. Plants of the new *Spathiphyllum* are more compact and slower-growing than plants of 'Domino'.
2. Plants of the new *Spathiphyllum* are not freely clumping whereas plants of 'Domino' are freely clumping.
3. Leaves of plants of the new *Spathiphyllum* are broader and more uniform in shape than leaves of plants of 'Domino'.
4. Leaves of plants of the new *Spathiphyllum* are not as undulate as leaves of plants of 'Domino'.
5. Plants of the new *Spathiphyllum* have variegated leaves that are yellow green to greyed green-in color with dark green-colored venation and margins whereas plants of 'Domino' have variegated leaves with white and green-colored random and variable sectors with green and white-colored midveins.
6. Plants of the new *Spathiphyllum* produce fewer but larger inflorescences than of plants of 'Domino'.

Plants of the new *Spathiphyllum* can also be compared to plants of *Spathiphyllum* Schott. 'Spadulu', disclosed in U.S. Plant Pat. No. 22,599. In side-by-side comparisons, plants of the new *Spathiphyllum* differ from plants of 'Spadulu' in the following characteristics:

1. Plants of the new *Spathiphyllum* are more compact and slower-growing than plants of 'Spadulu'.
2. Plants of the new *Spathiphyllum* are not freely clumping whereas plants of 'Spadulu' are freely clumping.
3. Leaves of plants of the new *Spathiphyllum* are smaller than leaves of plants of 'Spadulu'.
4. Plants of the new *Spathiphyllum* have variegated leaves that are yellow green to greyed green-in color with dark green-colored venation and margins whereas plants of 'Spadulu' have non-variegated leaves that are dark green in color.
5. Plants of the new *Spathiphyllum* produce fewer inflorescences than of plants of 'Spadulu'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet (FIG. 1) is a side perspective view of a typical young plant of 'Mukjess' grown in a container and is about 15 months from planting.

Figure 2:
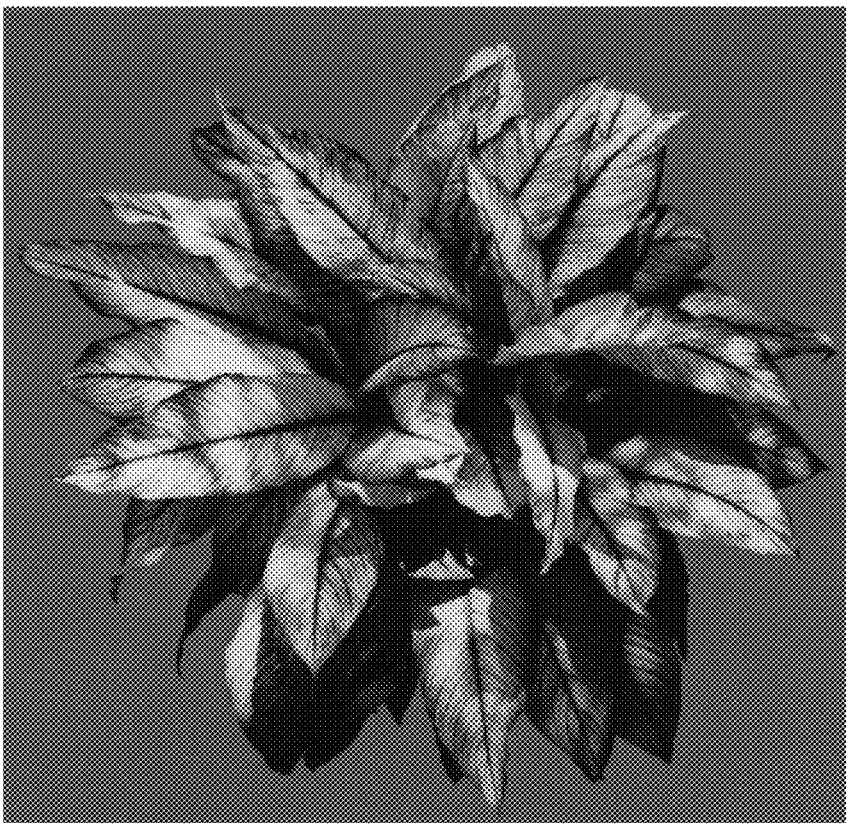

The photograph on the second sheet (FIG. 2) is a side perspective view of a typical older plant of 'Mukjess' grown in a container and is about 24 months from planting.

Figure 3:
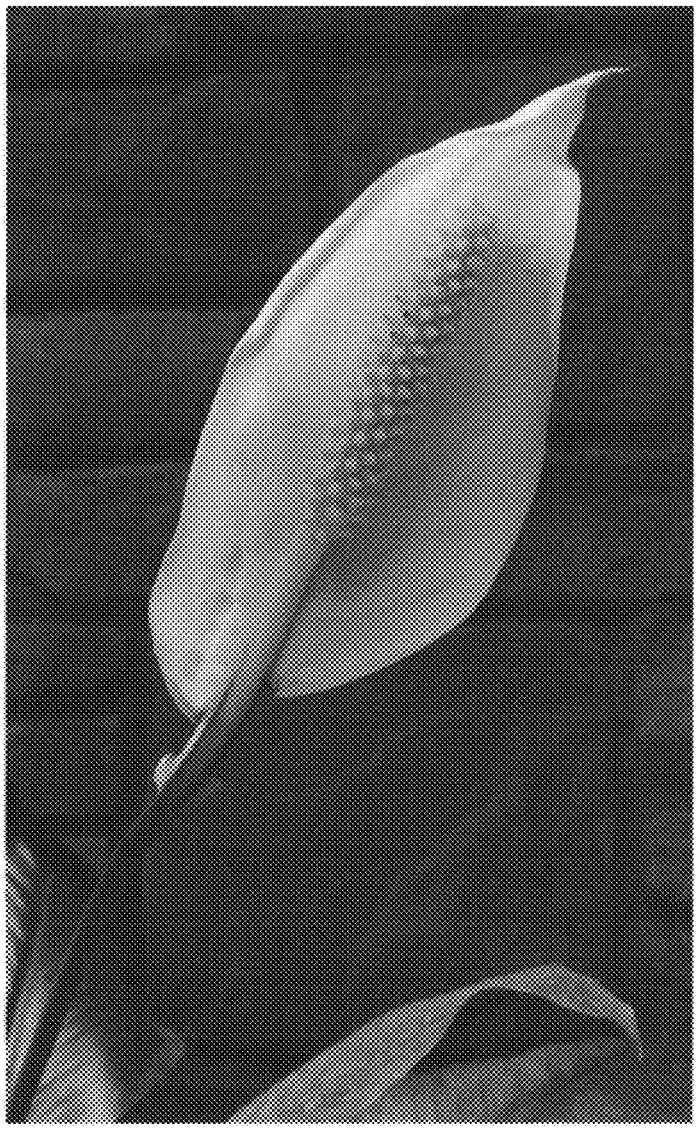

The photograph on the third sheet (FIG. 3) is a close-up view of a typical inflorescence of 'Mukjess'.

DETAILED BOTANICAL DESCRIPTION

The aforementioned photographs and following observations and measurements describe plants grown during the late winter to mid-summer in 20-cm containers in shadehouses in Miami, Fla. and Fort Worth, Tex. and under cultural practices typical of commercial *Spathiphyllum* production. During the production of the plants, day temperatures ranged from 16° C. to 35° C. and night temperatures ranged from 8° C. to 22° C. Plants were two years from transplanting rooted young plants when the detailed description was taken. In the following description, color references are made to The Royal Horticultural Society Colour Chart, 2015 Edition, except where general terms of ordinary dictionary significance are used.

Botanical classification: *Spathiphyllum* Schott. 'Mukjess'.

Parentage: Naturally-occurring whole plant mutation of an unnamed selection of *Spathiphyllum* Schott., not patented.

Propagation:

*Type.*—By in vitro meristem culture.

*Time to initiate roots.*—About two weeks.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately branching, medium density.

Plant description:

*Plant and growth habit.*—Relatively compact, upright, outwardly arching and uniform plant habit; overall plant shape, broadly inverted triangle; moderately vigorous growth habit and slow to moderate growth rate.

*Clumping habit.*—To date, plants of the new *Spathiphyllum* have not been observed to be freely clumping.

*Plant height, from soil level to top of leaf plane.*—About 63 cm.

*Plant height, from soil level to top of inflorescences.*—About 92 cm.

*Plant diameter or spread.*—About 89.5 cm.

*Stem description.*—Aspect: Mostly upright. Strength: Strong, somewhat flexible. Length: About 12.5 cm. Diameter at the base: About 2.5 cm. Internode length at the base: About 1.75 cm. Color: Darker than 147A.

*Leaf description.*—Arrangement: Alternate; simple. Length: About 35 cm. Width: About 18.5 cm. Shape: Elliptic. Apex: Acute to acuminate with short aristate tip, apex reflexed. Base: Obtuse. Margin: Entire; somewhat undulate; not lobed. Texture and luster, upper surface: Smooth, glabrous; moderately glossy. Texture and luster, lower surface: Smooth, glabrous; matte. Venation pattern: Pinnate. Color: Developing leaves, upper surface: Ground color, close to 189B, 189C, 189D and N155A; midvein and lateral veins, darker green than 147A. Developing leaves, lower surface: Ground color, close to NN155C and NN155D; midvein and lateral veins, close to 147B. Fully expanded leaves, upper surface: Ground color, close to 189C, 189D, NN155C and NN155D; midvein and lateral veins, darker green than 147A; with development, ground color becoming closer to 154C to 154D. Fully expanded leaves, lower surface: Ground color, close to NN155C and NN155D; midvein and lateral veins, close to 147B, 144A and 144C. Petioles: Length: About 26 cm. Diameter, distally: About 8 mm by 15 mm. Diameter, proximally, flattened: About 4.25 cm. Strength: Strong, flexible. Aspect: Mostly erect to somewhat outwardly arching with development. Texture and luster, upper and lower surfaces: Smooth, glabrous; matte. Color, upper surface: Distally, close to 147A; proximally, close to 145D. Color, lower surface:

Distally, close to 147A; proximally, close to 146A. Wing length: About 26 cm. Wing width: About 1 cm. Wing texture and luster, upper and lower surfaces: Smooth, glabrous; matte. Wing color, upper and lower surfaces: Close to 143B. Wing length: About 10.1 cm. Wing diameter: About 5 mm. Wing color, upper surface: Distally, close to 147A; proximally, close to 145D. Wing color, lower surface: Distally, close to 147A; proximally, close to 146A.

Inflorescence description:

*Inflorescence arrangement and flowering habit*.—If present, hooded spathes cupping a columnar spadix; inflorescences held above the foliar plane on strong and erect scapes; inflorescences axillary; spadix with sessile, simple female and male flowers separated into two zones with female flowers developing towards the base of the spadix and male flowers developing distally on the spadix.

*Fragrance*.—Faintly fragrant; fragrance, sweet and pleasant.

*Inflorescence longevity*.—Inflorescences last more than three weeks on the plant; inflorescences persistent.

*Spathe*.—Length: About 20 cm. Width, flattened: About 8.5 cm. Shape: Elliptic. Apex: Acuminate. Base: Attenuate. Margin: Entire. Texture and luster, front and rear surfaces: Smooth, glabrous; moderately glossy. Color: Front surface: Close to NN155D; with development, color becoming closer to 144A with random sectors, close to 157A. Rear surface: Close to NN155D; with development, color becoming closer to 144A.

*Spadix*.—Length, overall: About 8 cm. Length, female flower zone: Close to 4 cm. Length, male flower zone: Close to 4 cm. Diameter, female flower zone: Close to 6.5 mm. Diameter, male flower zone: Close to 6 mm. Shape: Columnar; apex, obtuse; base, obtuse; cross-section, circular. Aspect: Upright. Color, female and male flower zones, overall: Close to 157A; color becoming closer to 144A to 144B with development. Female flowers: Quantity per spadix: Numerous, about 240. Shape: Ovoid, pyramidal. Height: About 5 mm. Diameter: About 4 mm. Stigma color: Close to 150D. Ovary color: Close to 144B. Male flowers: Quantity per spadix: Numerous, about 225. Shape: Dumbbell-shaped. Height: About 1.5 mm. Diameter: About 1 mm. Pollen: None observed.

*Scapes*.—Length: About 54 cm. Diameter: About 7 mm. Strength: Sturdy, flexible. Aspect: Upright. Texture and luster: Smooth, glabrous; slightly glossy. Color: Close to 147A.

*Seeds and fruits*.—To date, seed and fruit development have not been observed on plants of the new *Spathiphyllum*.

Pathogen & pest resistance: To date, plants of the new *Spathiphyllum* have not been observed to be resistant to pathogens or pests common to *Spathiphyllum* plants.

Temperature tolerance: Plants of the new *Spathiphyllum* have been observed to be tolerant to temperatures ranging from about 8° C. to about 40° C. and to be suitable for USDA Hardiness Zones 10 to 13.

It is claimed:

1. A new and distinct *Spathiphyllum* plant named 'Mukjess' as illustrated and described.

* * * * *